United States Patent
Phillips et al.

(10) Patent No.: US 6,790,177 B2
(45) Date of Patent: *Sep. 14, 2004

(54) SURGICAL RETRACTOR APPARATUS

(75) Inventors: Burns Phillips, Nashville, TN (US); Larry Griffith, Lakeville, MN (US)

(73) Assignee: Boss Instruments, Ltd., Hermitage, TN (US)

(*) Notice: Subject to any disclaimer, the term of this patent is extended or adjusted under 35 U.S.C. 154(b) by 1 day.

This patent is subject to a terminal disclaimer.

(21) Appl. No.: 10/271,803

(22) Filed: Oct. 16, 2002

(65) Prior Publication Data

US 2004/0002633 A1 Jan. 1, 2004

Related U.S. Application Data

(63) Continuation-in-part of application No. 10/184,199, filed on Jun. 27, 2002, now Pat. No. 6,645,141.

(51) Int. Cl.⁷ .............................. A61B 1/32; E04G 7/00
(52) U.S. Cl. ....................... 600/228; 403/385; 403/389; 403/DIG. 9
(58) Field of Search ................................ 600/227, 228, 600/231–234; 403/385, 389, 390, 391, DIG. 9

(56) References Cited

U.S. PATENT DOCUMENTS

| | | | | |
|---|---|---|---|---|
| 2,893,378 A | * | 7/1959 | Cooper | 600/233 |
| 4,718,151 A | * | 1/1988 | LeVahn et al. | 24/535 |
| 4,993,862 A | * | 2/1991 | Pelta | 403/59 |
| 5,888,197 A | * | 3/1999 | Mulac et al. | 600/234 |
| 5,899,627 A | * | 5/1999 | Dobrovolny | 403/391 |
| 6,017,008 A | * | 1/2000 | Farley | 248/229.21 |
| 6,645,141 B1 | * | 11/2003 | Phillips et al. | 600/228 |

* cited by examiner

Primary Examiner—Pedro Philogene
Assistant Examiner—David A Bonderer
(74) Attorney, Agent, or Firm—Stephen J. Stark; Miller & Martin PLLC

(57) ABSTRACT

Surgical retractor apparatus is shown having at least two independently operable clamping locations for receiving pivot balls therein. These two clamping locations lock and unlock their respective pivot balls independent of locking of the other pivot ball. Furthermore, the locking mechanisms utilized to lock the pivot balls also utilize the lock the angular position of the extension rod relative to the clamp. An adjuster intermediate the clamping positions allows for the movement of the clamping location relative to each other.

20 Claims, 2 Drawing Sheets

SURGICAL RETRACTOR APPARATUS

CLAIM OF PRIORITY

This application is a continuation-in-part of U.S. patent application Ser. No. 10/184,199 filed Jun. 27, 2002, now U.S. Pat. No. 6,645,141

BACKGROUND OF THE INVENTION

1. Field of the Invention

The present invention relates generally to a surgical retractor apparatus. More particularly, the present invention relates to a retractor support coupler for use as a retractor support apparatus with a plurality of retractor support arms connected thereto.

2. Description of Related Art

U.S. Pat. No. 6,264,396, incorporated herein by reference, shows a clamp manufactured by Minnesota Scientific Inc. The arms have pivot balls thereon and the arms are often described having a "wishbone" shape as shown in FIG. 1. The pivot balls of this clamp only allow for the adjustment of the arms relative to the clamp. There does not appear to be any way to adjust the clamp position relative to the wound once the position of the clamp relative to the extension rod is selected. Furthermore, the clamp simultaneously locks two pivot balls upon the application of a single force. Clamping of one arm independent of the other arm is not possible.

U.S. Pat. No. 4,461,284 shows another surgical clamp device accepting two pivot balls and allowing for movement of the clamping locations relative to one another. However, there is no teaching in this reference for connecting a third arm or rod to this clamp. Additionally this reference teaches the application of a single force to secure two pivot balls at the same time.

Improvements over these designs are believed to be necessary.

SUMMARY OF THE INVENTION

A need exists to be able to independently lock one of two pivot balls independently of locking the other.

Furthermore, a need exists for the ability to lock the position of one pivot ball in a first clamping location as well as retaining the position of the clamp relative to the extension arm while still being able to position the other pivot ball relative to a second clamping location and then lock the same.

Another need exists to be able to adjust the spacing the location of the clamping positions relative to each other. This allows a single apparatus to be utilized for a variety of widths of incisions while using a relatively few number of arms sizes.

Accordingly, a surgical retractor apparatus is disclosed having at least two independently operable clamping locations for receiving pivot balls therein. These two clamping locations lock and unlock their respective pivot ball independent of the locking of the other pivot ball. Furthermore, the locking mechanisms utilized to lock the pivot balls are preferably also utilized together to lock the angular position of the extension rod relative to the clamp. An adjuster allows for the selective spacing of the clamping locations relative to each other.

BRIEF SUMMARY OF THE DRAWINGS

The particular features and advantages of the invention as well as other objects will become apparent from the following description taken in connection with the accompanying drawings in which.

DETAILED DESCRIPTION OF THE DRAWINGS

Figure 1:
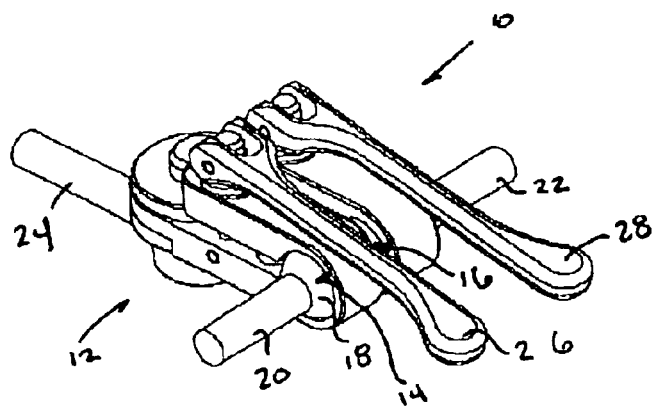
FIG. 1 is a top perspective view of a retractor support assembly of the preferred embodiment of the present invention.

FIGS. 1–4 show a retractor support apparatus 10 of the preferred embodiment. The retractor support apparatus 10 is particularly well suited for use with mounting surgical instruments, particularly retractors, with respect to an operating table as shown and described in U.S. Pat. No. 6,264,396 incorporated by reference. In fact, it is anticipated that the apparatus 10 shown herein has certain novel features which will provide advantages over the prior art.

The retractor support apparatus 10 of the preferred embodiment has a coupler 12 comprised of two independently operable clamping locations 14,16 as will be described in more detail below. First and second clamping locations 14,16 respectively, retain pivot balls 18 therein. Support arms 20,22 connect to the pivot balls 18. Extension rod 24 is connected to the coupler as shown. Retractors (not shown) are connected to the support arms 20,22 while the extension rod 24 is connected to a fixed support such as an operating table or otherwise.

The coupler 12 has a number of advantages over the prior art. First, the clamping locations 14,16 can be operated independently of one another. Thus, one pivot ball 18 may be locked in position while still allowing the other pivot ball 18 the ability to be rotated within the clamping location 14 or 16 without the other pivot ball 18 inadvertently moving during this procedure.

Additionally, when a single pivot ball 18 is locked in the first clamping position 14, the coupler 12 is preferably constructed so that at least the second clamping location 16 is movable relative to the extension rod 24. Furthermore, in the preferred embodiment, the first clamping location 14 is retained in a "set" position, but not locked relative to the extension rod 24 when the clamping location 14 has secured a pivot ball 18, and its associated pivot arm 20 at a desired angular orientation. Operators 26,28 are utilized to place the first and second clamping locations 14,16 respectively, in a locked configuration. Furthermore, the operators 26,28, when utilized together, may be utilized to secure the extension rod 24 in a fixed angular position relative to the coupler 12 as will be described in further detail below.

Figure 2:
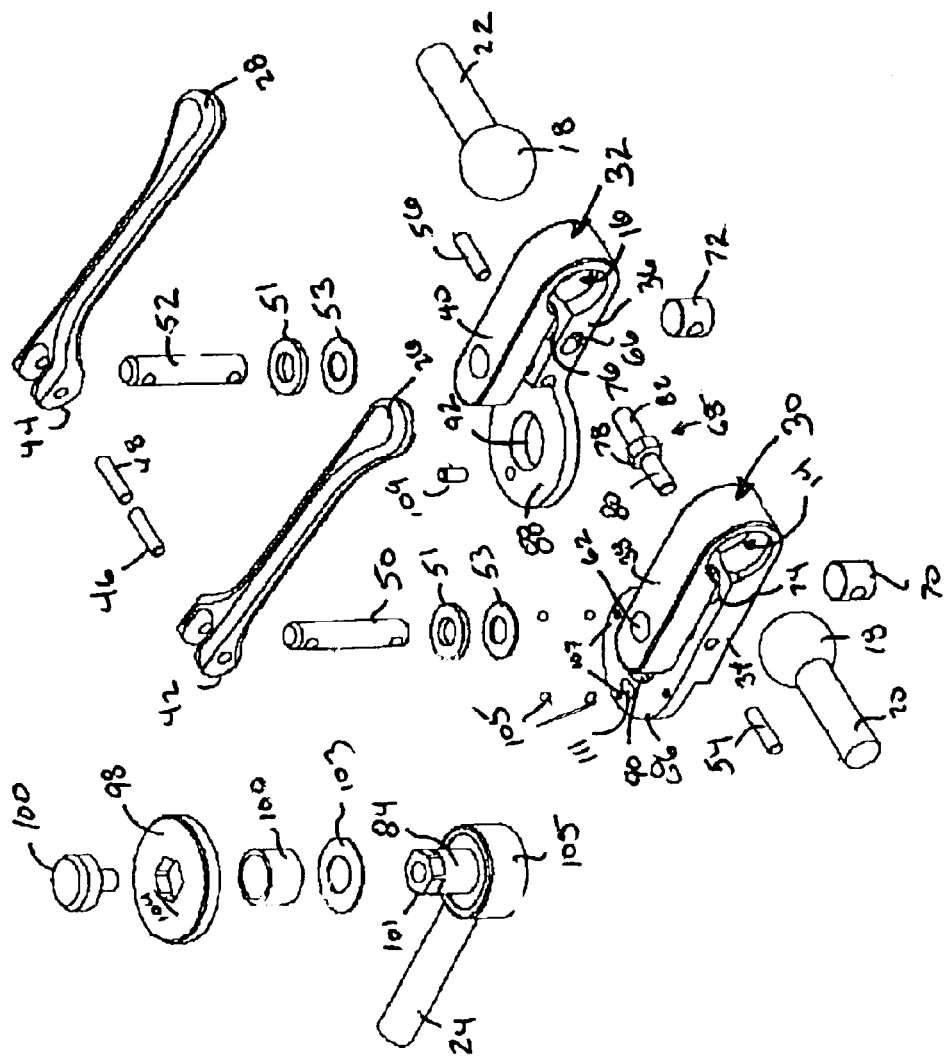
FIG. 2 is an exploded diagrammic view of the components which comprise the retractor support assembly of FIG. 1.

In order to understand the operation of the retractor support apparatus 10, it is helpful to examine the individual parts shown in the exploded view of FIG. 2. The retractor support apparatus 10 is comprised of first and second separate clamps 30,32. The clamps 30,32 each have clamping locations 14,16 for respectively accepting a pivot ball 18 therein. The clamps 30,32 have a body 34,36 connected to legs 38,40, respectively. As operators 26,28 are rotated, cam surfaces 42,44 act on legs 38,40 to push the legs closer to the bodies 34,36 and thus lock the clamping locations 14,16 with the pivot balls 18 therein. The clamping locations 14,16 are located at a proximal end of the bodies 34,36 and legs 38,40.

The cam surfaces 42,44 rotate around pins 46,48 which provide a pivot point relative to posts 50,52. The posts 50,52 are connected respectively by pins 54,56 to the bodies 34,36. The cam surfaces 42,44 preferably act on cam nest washers 58,60 located on top of the legs 38,40. The posts 50,52 are received within bores 62,64 located in both the legs 38,40 and body 34,36. The cam surfaces 42,44 have a changing radius over a curved surface so that as the respective operator 26,28 rotates, the distal end of the leg 38,40 is pushed toward the body 34,36 and lock a pivot ball 18 within a clamping location 14,16. While two operators 26,28 are utilized with the preferred embodiment, a single operator could be utilized in other embodiments. Washers 51 and springs 53 are utilized in the preferred embodiment to assist in the operation and/or biasing of the operators 26,28.

One advantage of the preferred embodiment is the ability to move the clamping locations 14,16 relative to each other. Bores 66 receive the adjuster 68 which inserts 70,72 which are located in cut outs 74,76 in the bodies 34,36. The inserts preferably have round exterior surfaces which allow the adjuster 68 to move the bodies 34,36 and thus the clamping portions 14,16 support and away from another one without binding occurring since the bodies 34,36 can rotate relative to the inserts 70,72. The adjuster 68 preferably has a nut 78 and threaded portions 80,82 which are received in the inserts 70,72. This is believed to assist in providing precise placement of the clamping locations 14,16 at desired locations.

As the bodies 34,36 are moved toward or away from one another with the adjuster 68 at the inserts 70,72, the clamping locations 14,16 rotate about the hub 84. Disc portions 86,88 are able to rotate relative to one another and still provide a stable platform for securing the extension rod 24 relative to the clamping locations 14,16. The disc portions 86,88 have bores 90,92 which receive hub 84 therethrough. The disc portions 86,88 rotate about hub 84.

Figure 3:
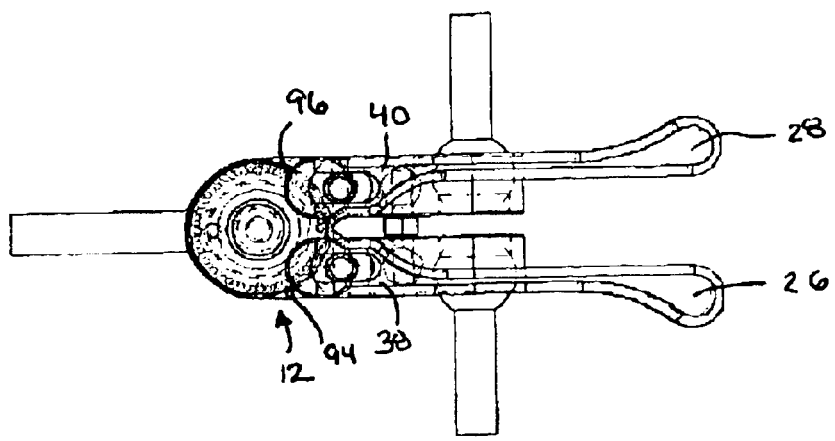
FIG. 3 is a top plan view of the retractor support assembly of FIG. 1 with internal portions shown in phantom.
Figure 4:
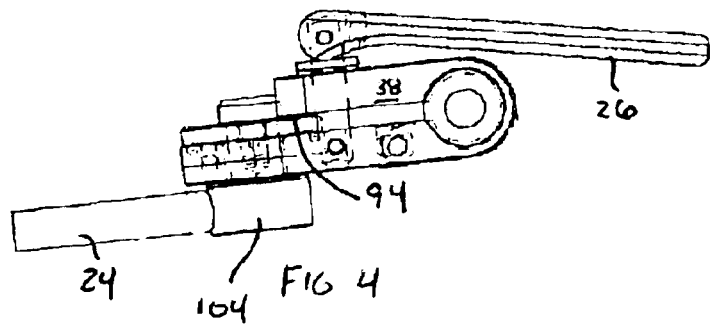
FIG. 4 is a side plan view of the retractor support assembly of FIG. 1 with internal portions shown in phantom.

In order to lock the position of the coupler 12 relative to the extension rod 24, the operators 26,28 engage their respective leg 38,40. As the legs 38,40 are pushed downwardly, locking surfaces 94,96 (partially obscured from view) as seen in FIG. 3 contact head 98 which is preferably fixably mounted to hub 84 with a cap 100. Sleeve 102 spaces the head 98 at the nut 101 so that the head 98 preferably does not rotate relative to the extension rod 24. The sleeve 102 passes through bores 90,92 in the discs 86,88. Spring 103 biases disks 86,88 against head 98 so that the relative rotational position of disks 86,88 relative to one another resists movement, but can be overcome, as well. Bearings 105 intermediate the top disk 88 and a bottom surface of head 98 provide for smooth angular adjustment of the disks 86,88. The bearings 105 are inset in recesses 107.

As the legs 38,40 are forced downwardly by operation of the operators 26,28 respectively, the locking surfaces 94,96 at the distal end of the legs 38,40 contact face 104 of head 98. When only one of the locking surfaces 94,96 engaged the head 98, the angular position of the extension rod 24 relative to the coupler 12 is preferably "set" but not locked. Accordingly, the coupler 12 may be twisted relative to the extension rod 24 with the application with sufficient force. However, when the second of the two operators 26,28 is placed in a locking position with the locking surfaces 94,96 in contact with the head 98, the angular position of the extension rod 24 relative to the coupler 12 may be locked. Dowel 109 which travels in slot 111 may provide stability to the coupler 12 during angular adjustment of the clamping areas 14,16 relative to one another.

With proper selection of the tolerances and spacing of the disc portions 86,88 relative to the head 98 and the locking surfaces 94,96 relative to the face 104, the operation of a single operator 26 or 28 locks the single leg 38 or 40 relative to the body 34 or 36 and sets the angular position of the extension rod 24 relative to the coupler 12. This "setting" provides resistance, however, it does not lock the extension rod 24 relative to the coupler 12 so that the position may still be adjusted with greater amount of force. However, once the second operator 26,28 is locked, the second locking surface 94,96 against the face 104 of the head 98 locks the position of the extension rod relative to the coupler 12 so that the attempted twisting of the coupler relative to the extension rod 24 will not be productive. Spring 103 has been found helpful in assisting in the "setting" and locking features of the extension rod 28 relative to the coupler 12.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A retractor support apparatus comprising:
    an extension rod;
    a first and second pivot arm with a pivot ball respectively attached thereto;
    a coupler operably coupled to the extension rod, the extension rod angularly adjustable relative to the coupler, said coupler having
    a first and second clamping location, said first clamping location receiving and engaging said pivot ball of said first pivot arm, said second clamping location receiving and engaging said pivot ball of said second pivot arm, said first clamping location having a locked and a non-locked position wherein when in said locked position said first pivot arm is held securely by the first clamping location, said second clamping location having a locked and a non-locked position wherein when in said locked position said second pivot arm is held securely by the second clamping location, and
    a head which cooperates with the first and second clamping locations to fixedly set the angular position of the extension rod relative to the coupler when the first and second clamping locations are in the locked position.

2. The retractor support apparatus of claim 1 wherein the first clamping location has a moveable leg, and the leg has a locking surface which contacts the head, when in the locked position.

3. The retractor support apparatus of claim 2 wherein the locking surface does not contact the head when in the non-locked position.

4. The retractor support apparatus of claim 2 wherein the second clamping location has a moveable leg, and the leg has a locking surface which contacts the head when in the locked position.

5. The retractor support apparatus of claim 4 wherein the locking surface of the leg of the second clamping location does not contact the head when in the non-locked position.

6. The retractor support apparatus of claim 1 wherein the head is disc shaped.

7. The retractor support apparatus of claim 1 wherein the clamping locations further comprise body members connected to disc portions, and the disc portions are restrained from rotation relative from one another in the locked position and rotationally moveable relative to one another in the non-locked position.

8. The retractor support apparatus of claim 7 wherein the disc portions have bores extending therethrough, and further comprising a hub which extends through the bores of the disc portions.

9. The retractor support apparatus of claim 7 wherein the head is retained to the hub by a cap.

10. The retractor support apparatus of claim 7 further comprising bearings intermediate the disc portion of the first clamping location and the head.

11. The retractor support apparatus of claim 10 wherein the disc portion has recesses which receive the bearings.

12. A retractor support apparatus comprising:
   an extension rod;
   a first and second pivot arm with a pivot ball respectively attached thereto;
   a coupler operably coupled to the extension rod, said coupler having
   a first and second clamping locations each respectively defined intermediate a body and a leg, said first clamping location receiving and engaging said pivot ball of said first pivot arm, said second clamping location receiving and engaging said pivot ball of said second pivot arm, said first clamping location having a locked and a non-locked position wherein when in said locked position said first pivot arm is held securely by the first clamping location, said second clamping location having a locked and a non-locked position wherein when in said locked position said second pivot arm is held securely by the second clamping location, said first and second clamping locations pivotable relative to one another about a pivot when in the non-locked position, and
   a head which assists in retaining the extension rod relative to the first and second clamping locations when at least one of the first and second clamping locations is in the locked position.

13. The retractor support apparatus of claim 12 wherein the first and second clamping locations further comprise disc portions connected to the body members which are clamped together when in the locked position.

14. The retractor support apparatus of claim 13 wherein the discs move linearly intermediate the locked and non-locked positions.

15. The retractor support apparatus of claim 14 wherein the head moves linearly from the non-locked to the locked position.

16. The retractor support apparatus of claim 13 wherein the head is disc shaped.

17. The retractor support apparatus of claim 13 further comprising bearings intermediate the head and the disc connected to the body member of the first connection portion.

18. The retractor support apparatus of claim 17 wherein the disc has recesses which receive the bearings at least partially therein.

19. The retractor support apparatus of claim 12 wherein the second leg has a locking surface which contacts the head in a locked configuration and locks the angular position of the extension rod relative to the second leg.

20. The retractor support apparatus of claim 19 wherein the first leg has a locking surface which contacts the head in a locked configuration and locks the angular position of the extension rod relative to the first leg.

* * * * *